(12) United States Patent
Asahina

(10) Patent No.: US 6,541,748 B1
(45) Date of Patent: Apr. 1, 2003

(54) OPTICAL DISK CHECKUP/MEASURING APPARATUS

(75) Inventor: Takayuki Asahina, Shizuoka (JP)

(73) Assignee: Sony Disc Technology Inc., Tokyo (JP)

( * ) Notice: Subject to any disclaimer, the term of this patent is extended or adjusted under 35 U.S.C. 154(b) by 0 days.

(21) Appl. No.: 09/500,581

(22) Filed: Feb. 10, 2000

(30) Foreign Application Priority Data

Feb. 16, 1999 (JP) ............................................. 11-037582

(51) Int. Cl.⁷ ................................................. G11B 7/00
(52) U.S. Cl. .............................. 250/201.5; 250/201.2; 369/44.35
(58) Field of Search .......................... 250/201.5, 201.4, 250/201.2, 201.1, 205, 231.13; 369/44.13, 44.35, 44.37, 44.32, 44.41

(56) References Cited

U.S. PATENT DOCUMENTS 5,559,771 A * 9/1996 Kim ........................ 369/44.35
5,572,493 A * 11/1996 Maeda et al. ............. 369/44.28

* cited by examiner

Primary Examiner—Kevin Pyo
(74) Attorney, Agent, or Firm—Jay H. Maioli

(57) ABSTRACT

An optical disk checkup/measuring apparatus capable of shortening measuring time and of being incorporated into a manufacturing line and has a simple structure includes rotation driving elements (2,3) for driving rotation of an optical disk to be measured (10), a light emitting portion LD for emitting a light beam LF onto the optical disk to be measured (10), an optically detecting portion (D1, D2) for receiving and detecting the light beam LR reflected from the optical disk to be measured (10) and an operation processing portion (4, 5) for processing a signal received and detected by the optically detecting portion (D1, D2) so as to form a specified signal. The light emitting portion is composed of a plurality of light emitting elements LD provided in a radial direction of the optical disk to be measured (10), and the light beams are emitted successively from the light emitting elements LD onto the optical disk to be measured (10).

3 Claims, 4 Drawing Sheets

OPTICAL DISK CHECKUP/MEASURING APPARATUS

BACKGROUND OF THE INVENTION

1. Technical Field

The present invention relates to an optical disk checkup/measuring apparatus for measuring birefringence, skew and the like on an optical disk.

2. Description of the Related Art

Usually, an optical disk manufactured in a factory is checked in such a manner that properties of the optical disc such as birefringence, skew and the like are measured by using an optical disk checkup/measuring apparatus.

Conventionally, such a kind of the checkup/measuring apparatus is composed of one laser diode as a light emitting source and a pair of photodetectors as light receiving/detecting elements, and the one laser diode and the pair of photodetectors are moved by a set width to a radial direction of the optical disk so that measurement is made.

Furthermore, in the case where measurement in a rotating direction of an optical disk is necessary, the optical disk on a turntable is rotated so that measurement is made in the same manner.

With this measuring method, it took a long time to measure the whole surface of the optical disk.

Since the measuring time was greatly longer than a cycle at the time of manufacturing a disk, it was impossible that a checkup/measuring apparatus is incorporated into an optical disk manufacturing apparatus so that the measuring is made on the manufacturing line.

In addition, since a mechanism for accurately cross feeding is required for moving an optical system such as the laser diode and photodetectors to the radial direction of the optical disk, the checkup/measuring apparatus has a complicated mechanism.

SUMMARY OF THE INVENTION

In order to solve the above problem, the present invention provides an optical disk checkup/measuring apparatus having a simple structure which is capable of shortening measuring time and of being incorporated into a manufacturing line.

An optical disk checkup/measuring apparatus according to the present invention includes: rotation driving means for driving rotation of an optical disk to be measured; a light emitting portion for emitting a light beam onto the optical disk to be measured; an optically detecting portion for receiving and detecting the light beam reflected from the optical disk to be measured; and an operation processing portion for operating a signal received and detected by the optically detecting portion so as to form a specified signal, wherein the light emitting portion is composed of a plurality of light emitting elements provided in a radial direction of the optical disk to be measured, and the light beams are emitted successively from the respective light emitting elements onto the optical disk to be measured.

According to the above constitution of the present invention, since the light emitting portion is composed of a plurality of light emitting elements provided in the radial direction of the optical disk to be measured, a mechanism for moving the light emitting portion and optically detecting portion to the radial direction is not required, and the measurement is repeated in a state that the optical disk to be measured is driven to be rotated by the rotation driving means so that the whole periphery of the optical disk to be measured can be measured.

BRIEF DESCRIPTION OF THE DRAWINGS

FIG. 3 is a diagram (cross section of an optical disk in its radial direction) showing a constitution of an optical system to be used in the optical disk checkup/measuring apparatus in FIG. 1 and in the optical disk checkup/measuring apparatus in FIG. 2:

DETAILED DESCRIPTION OF THE PREFERRED EMBODIMENT

The present invention is an optical disk checkup/measuring apparatus which includes rotation driving means for driving rotation of an optical disk to be measured, a light emitting portion for emitting a light beam onto the optical disk to be measured, an optically detecting portion for receiving and detecting the light beam reflected from the optical disk to be measured and an operation processing portion for processing a signal which was received and detected by the optically detecting portion so as to form a specified signal. The light emitting portion is composed of a plurality of light emitting elements provided in a radial direction of the optical disk and the light beams are emitted successively from the respective light emitting elements onto the optical disk to be measured.

In addition, the present invention is the optical disk checkup/measuring apparatus which is constituted so that at least one of birefringence and skew is measured for the optical disk to be measured.

Further, the present invention is the optical disk checkup/measuring apparatus which is constituted so that the light emitting elements are excited one by one from one direction of the radial direction and the light beams are emitted successively from the respective light emitting elements onto the optical disk to be measured.

Furthermore, the present invention is the optical disk checkup/measuring apparatus which is constituted so that a shutter is provided between the light emitting portion and the optical disk to be measured, and when the shutter is opened or closed in a state that the lights are emitted from all the light emitting elements, the light beams are emitted successively from each of the light emitting elements onto the optical disk to be measured.

In addition, the present invention is the optical disk checkup/measuring apparatus which is constituted so that a plurality of light emitting element files composed of plural light emitting elements are formed, and the plurality of light emitting element files are shifted from each other in the radial direction so as to be arranged in a direction where the optical disk is driven to be rotated.

Further, the present invention is the optical disk checkup/measuring apparatus which is constituted so that a plurality of the light emitting element files composed of plural light emitting elements are formed and at least one light emitting file is arranged in each of areas obtained in such a manner that the whole periphery of the optical disk to be measured is divided by equal angle.

Figure 1:
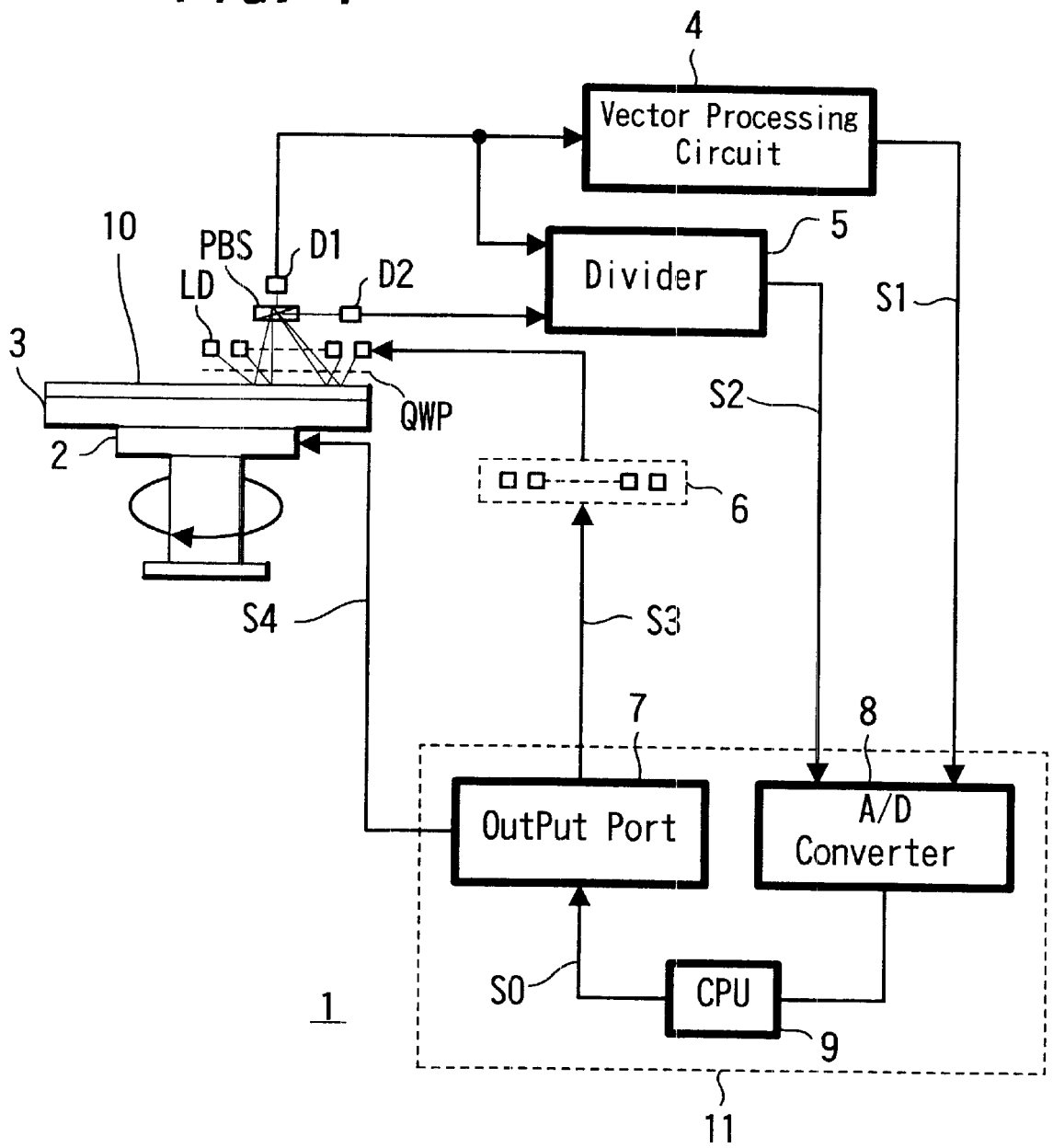
FIG. 1 is a schematic constitutional diagram showing an optical disk checkup/measuring apparatus according to one embodiment of the present invention.

FIG. 1 shows a schematic constitutional diagram of the optical disk checkup/measuring apparatus according to one embodiment of the present invention.

The optical disk checkup/measuring apparatus 1 has a motor 2 as rotation driving means and a turn table 3 on the motor 2, and an optical disk 10 to be measured is placed on the turn table 3.

At the time of check and measurement, the motor 2 is driven and rotated fully once so that the optical disk 10 to be measured is rotated fully once.

A plurality of laser diodes LD, which are provided in the radial direction of the optical disk 10 as light emitting elements composing the light emitting portion, are provided above the optical disk 10 to be measured.

A quarter-wave plate QWP, a polarization beam splitter PBS, a first position detector D1 and second position detector D2 as light receiving elements composing the light receiving/detecting portion are provided correspondingly to the plural laser diodes LD.

In addition, thin lines in FIG. 1 represent an optical signal, and thick lines represent an electric signal.

As for the plurality of laser diodes LD, their directions are set to a specified angle so that the optical signals composed of laser beams generated respectively from the laser diodes LD are reflected from a reflecting surface of the optical disk 10 to be measured so as to go towards the center of the polarization beam splitter PBS.

The quarter-wave plate QWP is provided so as to separate the optical signal as a circular polarized light into two in the polarization beam splitter PBS.

As for the first position detector D1 and second position detector D2, axes of X direction and Y direction are taken respectively on their light receiving surfaces, and the first position detector D1 and second position detector D2 compose a position detecting sensor which is capable of detecting a change in the positions of optical axes of the laser beams.

The directions of the light receiving surfaces are set to a specified angle so that the optical signals, which came into the polarization beam splitter PBS so as to be separated, go towards the centers of the position detectors D1 and D2.

In addition, as the operation processing portion for processing the signals detected in the light receiving/detecting portion so as to form specified signals, a vector processing circuit 4 and a divider 5 are provided, and an LD power controller 6 for controlling the laser diodes LD, and a computer 11 for processing data and controlling an operation of the checkup/measuring apparatus 1 are provided.

Furthermore, an output port 7 for output, an A/D converter 8 and CPU 9 are provided in the computer 11.

The vector processing circuit 4 processes a detected signal from the first position detector D1 so as to generate a skew signal S1.

The divider 5 performs an operation based on the detected signals from the first position detector D1 and second position detector D2 so as to generate a birefringence signal S2.

The A/D converter 8 in the computer 11 converts the skew signal S1 and birefringence signal S2 into analog/digital signals so as to transmit the converted signals to the CPU 9.

The CPU 9 processes the A/D converted skew signal S1 and birefringence signal S2 so as to obtain a measured value and gives a control signal S0 to the output port 7. Then, the CPU 9 gives a laser control signal S3 to the LD power controller 6 and a motor control signal S4 to the motor 2 via the output port 7.

The LD power controller 6 applies a voltage to the laser diodes LD one by one from one direction of the radial direction of the optical disk 10 based on the laser control signal S3 so as to excite the laser diodes LD.

As a result, it is controlled such that the plurality of laser diodes LD emit lights one by one successively from one direction (inner side or outer side) of the radial direction of the optical disk 10 to be measured.

In addition, the motor 2 drives to rotate the optical disk 10 to be measured based on the motor control signal S4 so that the optical disk 10 rotates fully once at the time of measurement.

There will be described below an operation of the optical disk checkup/measuring apparatus 1.

At first, the LD power controller 6 allows the laser diodes LD which are provided in the radial direction of the optical disk 10 to emit a light one by one from one direction (inner side or outer side) based on the laser control signal S3 from the CPU 9 in the computer 11 so as to generate optical signals composed of laser beams.

The laser beam generated from the laser diode LD is transmitted through the quarter-wave plate QWP so as to become a circular polarized light, and is reflected from the reflecting surface of the optical disk 10 so as to come into the polarization beam splitter PBS. Then, the light is separated into beams of two directions by the polarization beam splitter PBS so as to come into the first position detector D1 and second position detector D2, respectively.

The first and second position detectors D1 and D2 receive the incident optical signals respectively so as to output detected signals. The detected signal of the first position detector D1 is transmitted to the vector processing circuit 4 and divider 5, and the detected signal of the second position detector D2 is transmitted to the divider 5.

The vector processing circuit 4 operates the detected signal of the first position detector D1 so as to output a skew signal S1.

Moreover, the divider 5 operates the detected signal of the first position detector D1 and the detected signal of the second position detector D2 so as to obtain a birefringence signal S2.

The skew signal S1 and birefringence signal S2 are transmitted to the computer 11. These signals are converted into digital signals by the A/D converter 8 in the computer 11 and are processed by the CPU 9 so that a measured value is obtained.

Here, one cycle of the measurement is completed. The measured values corresponding to a number of the laser diodes LD are obtained during one cycle.

The data on the obtained measured values are stored in a memory of the computer 11 or are outputted to a recording medium or a monitor of CRT or the like.

Next, the motor control signal S4 is given from the CPU 9 via the output port 7 to the motor 2 so that the motor 2 is driven to be rotated. As a result, the optical disk 10 to be measured is rotated so that the laser diodes LD move to a position where next measurement will be made.

Since time required for measurement in one cycle is short, the measurement may be made while the motor 2 is always being driven and the optical disk is being rotated. It is preferable that the motor 2 is always driven within the range that measuring accuracy is not deteriorated because the whole periphery can be measured for short time.

Hereinafter, the cycle is repeated until the measurement of the whole periphery of the optical disk 10 to be measured is completed while the optical disk 10 is rotated fully once.

The number of the cycles are defined by the number of places to be measured required for the check of the optical disk.

According to the optical disk checkup/measuring apparatus 1 according to the present embodiment, since a plurality of laser diodes LD are arranged in the radial direction of the optical disk 10 so that the measurement is made, it is not necessary to move the optical system to the radial direction, and thus the speed of the measurement of birefringence, skew and the like is heightened. As a result, the measuring time can be shortened in accordance with the speed of the manufacturing line of the optical disk.

Therefore, the optical disk checkup/measuring apparatus 1 is provided in an optical disk manufacturing apparatus so that the check and measurement can be made during the manufacturing process.

As a result, the number of steps of the checking operation can be reduced, and a defect can be found earlier.

In addition, in a conventional optical disk checkup/measuring apparatus, a moving mechanism of an optical system such as laser diodes, detectors and the like is required for measuring the whole surface of the disk, but with the optical disk checkup/measuring apparatus 1 according to the present embodiment, such a moving mechanism of the optical system is not required, and thus the structure is simplified.

Figure 2:
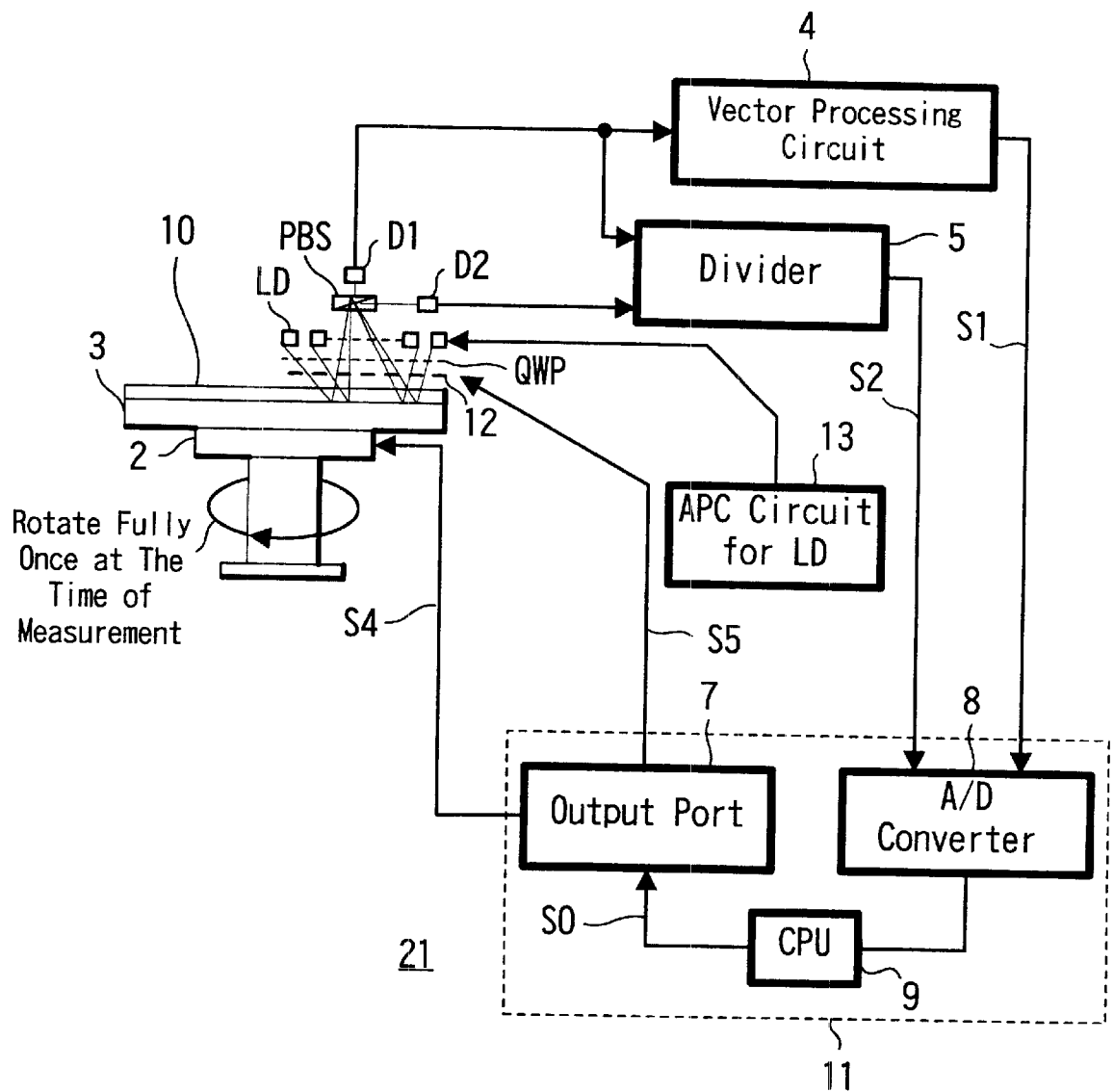
FIG. 2 is a schematic constitutional diagram showing the optical disk checkup/measuring apparatus according to another embodiment of the present invention.

FIG. 2 shows a schematic constitutional diagram of the optical disk checkup/measuring apparatus according to another embodiment of the present invention.

An optical disk checkup/measuring apparatus 21 is provided with a plurality of shutters 12 between the laser diodes LD and the optical disk 10 to be measured so that the shutters 12 have one to one correspondence to output terminals of the laser diodes LD arranged in the radial direction of the optical disk 10 to be measured.

The plurality of shutters 12 are controlled by a shutter control signal S5 given from the CPU 9 in the computer 11 via the output port 7 so as to be opened and closed.

In addition, the plurality of laser diodes LD are controlled by an APC (automatic output control) circuit 13 for LD.

In the present embodiment, particularly the laser diodes LD emit a light simultaneously, and the plurality of shutters 12 are opened and closed successively from one direction of the radial direction of the optical disk 10 to be measured. As a result, the laser beams from the laser diodes LD arranged in the radial direction of the disk come into the polarization beam splitter PBS one by one.

Since the other parts of the structure are similar to those of the optical disk checkup/measuring apparatus 1 shown in FIG. 1, the same reference numerals are given to them and the description thereof is omitted.

With the optical disk checkup/measuring apparatus 21 according to the present embodiment, similarly with the optical disk checkup/measuring apparatus 1, the measuring time required for measuring skew, birefringence and the like can be shortened, and the checkup/measuring apparatus 21 is provided in the optical disk manufacturing apparatus so that the number of the steps of the check can be reduced and a defect can be found earlier.

In addition, since a moving mechanism of the optical system is not required, the structure of the optical disk checkup/measuring apparatus can be simplified.

Figure 3A:
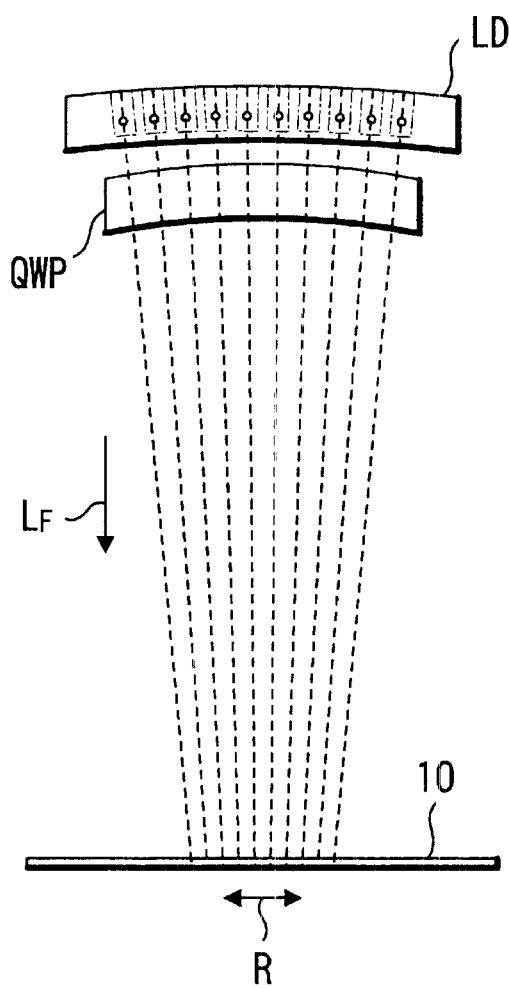
FIG. 3A is a diagram showing a constitution on the side of a laser diode.
Figure 3B:
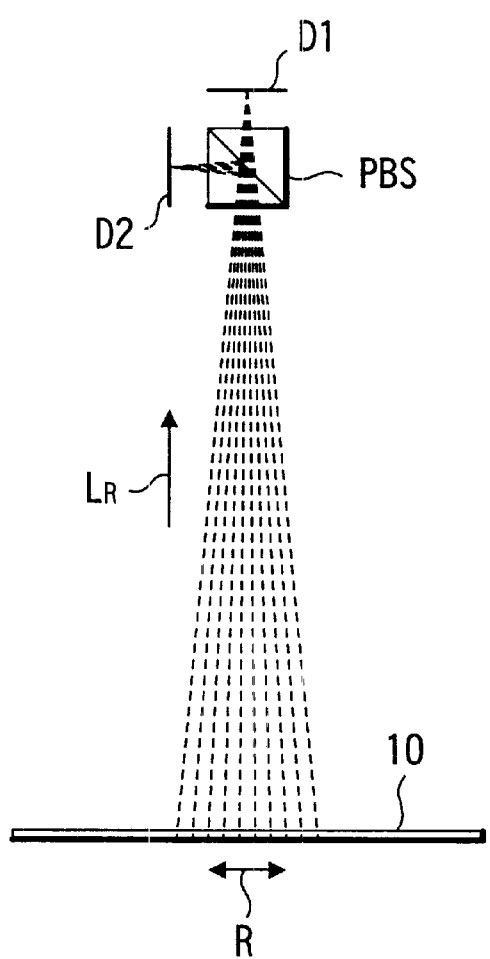
FIG. 3B is a diagram showing a constitution on the side of a detector.
Figure 4:
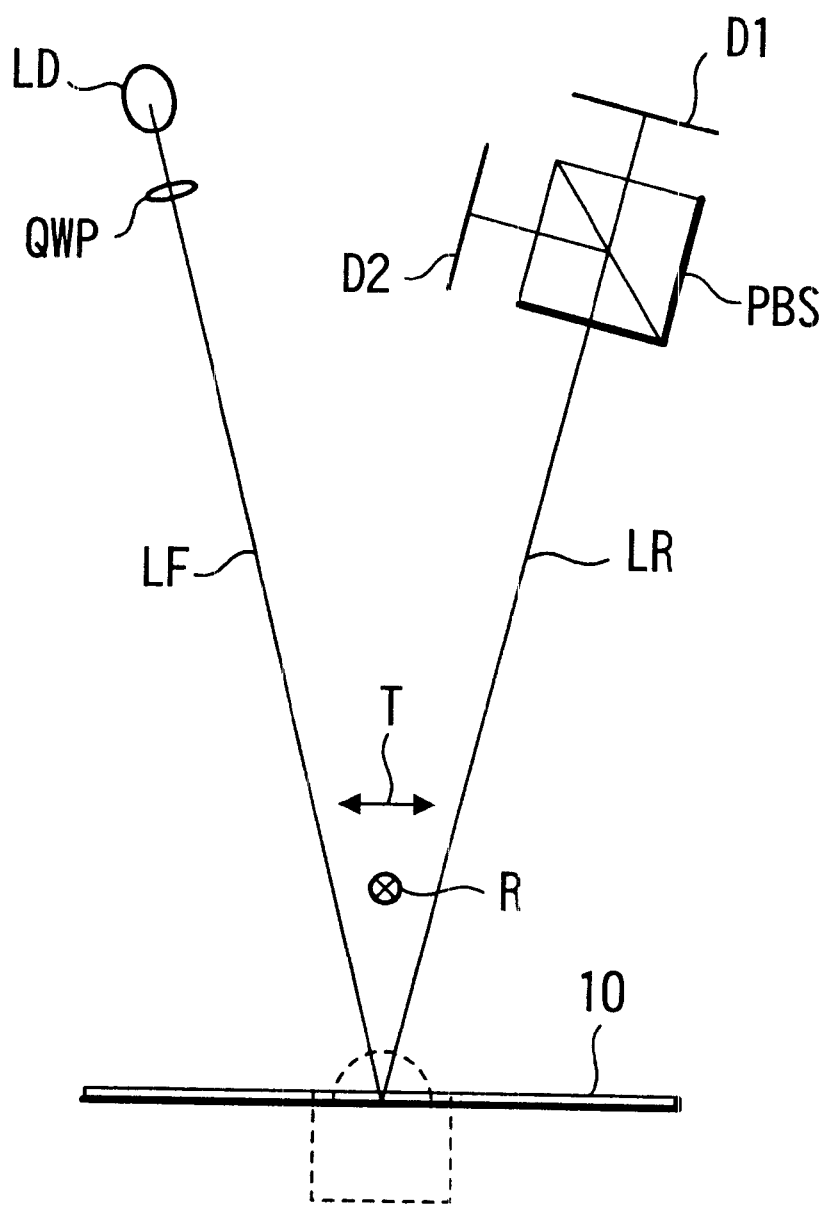
FIG. 4 is a diagram (cross section of the optical disk in its rotational direction) showing a constitution of the optical system to be used in the optical disk checkup/measuring apparatus in FIG. 1 and in the optical disk checkup/measuring apparatus in FIG. 2.

FIGS. 3 and 4 show a structure of the optical system to be used in the optical disk checkup/measuring apparatus 1 shown in FIG. 1 and the optical disk checkup/measuring apparatus 21 shown in FIG. 2.

FIG. 3A is a diagram showing the structure on a side of the laser diodes, and FIG. 3B is a diagram showing the structure on a side of the detectors, and both of them are cross sections of the radial direction R of the optical disk 10 to be measured. Moreover, FIG. 4 is a cross section of a rotating direction T of the optical disk 10 to be measured showing the whole structure of the optical system.

As shown in FIGS. 3 and 4, the laser beams (emitted lights LF) outputted from the laser diodes LD respectively are transmitted through the quarter-wave plate QWP and emitted to the reflecting layer of the optical disk 10 to be measured, and are reflected from the reflecting layer so as to come into the polarization beam splitter PBS.

The incident light is separated into two lights: one goes straight so as to come into the first position detector D1; and the other is bent at a right angle so as to come into the second position detector D2 in the polarization beam splitter PBS. The two lights are received and detected respectively by the position detectors D1 and D2.

As shown in FIG. 4, in order to make the light receiving and detection possible, emitting directions of the laser beams from the laser diodes LD, a direction of the polarization beam splitter PBS, and directions of the light receiving surfaces of the position detectors D1 and D2 are set so that they are specifically angled.

At this time, as shown in FIG. 3A, pencils of the laser beams are wholly converged to the radial direction R of the optical disk 10 to be measured.

When such a structure that the laser beams are converged is provided, as shown in FIG. 3B, the light (reflected light LR) which was reflected from the reflecting layer of the optical disk 10 to be measured is also converged so that the laser beams from the plurality of laser diodes LD can come into the one polarization beam splitter PBS.

In addition, since a length obtained by adding the plural laser diodes LD may be set to be longer than a width of a measuring area of the optical disk 10, the number of the laser diodes LD arranged in the radial direction R can be increased.

In FIG. 3A, the one quarter-wave plate QWP is provided, but every one quarter-wave plate QWP may be provided for each of the laser diodes LD.

In FIGS. 3 and 4, the light emitting element row is composed so that the laser diodes LD are arranged in a row in the radial direction R, but not less than two light emitting element files are arranged in the rotating direction T so as to be shifted from the radial direction R, and spaces of the laser diodes LD in the radial direction R is set to not more than ½.

In this case, since the number of the laser diodes in the radial direction.R can be increased twice or more, the number of measuring points can be increased without increasing the measuring time. This structure is effective particularly in the case where a laser unit composing the laser diodes LD is large-sized and the number of the laser diodes LD in the radial direction R cannot be increased very much.

In the above-mentioned embodiments, the optical system is positioned on one place of the optical disk 10 to be measured, but the optical system, which is composed of the laser diode LD files, the polarization beam splitter PBS and the position detectors D1 and D2, may be positioned in each of areas obtained in such a manner that the optical disk 10 is divided into n (n: natural numbers of not less than 2) by equal angle radially, for example.

In this case, the whole surface of the optical disk can be measured by 1/n revolution of the rotation and driving of the motor 2 at the time of measurement, and the repeating cycle becomes 1/n.

In addition, since n sets of the optical systems are required, the polarization beam splitter PBS and the position detectors D1 and D2 are provided in n places. Additionally, a structure is conceivable wherein the polarization beam splitter PBS and the position detectors D1 and D2 are provided so as to be gathered at the center, but this structure is not very preferable because an incident angle of the laser beams is close to the level.

Furthermore, files of n-set laser diodes LD positioned in each of the n-divided areas can be positioned so that the files of the laser diodes LD in the radial direction R are partially or wholly shifted. In this case, the rotation and driving of the motor 2 at the time of measurement increases larger than 1/n revolution, but time required for the rotation and driving barely increases.

Similarly to the above-mentioned case where two or more files of the laser diodes LD are arranged in the rotating direction, in this case the number of the laser diodes in the radial direction R can be increased so that the number of measuring points can be increased without increasing the measuring time.

The aforementioned embodiments referred to the structure that the birefringence and skew of the optical disk are measured, but there may be a structure wherein only one of the birefringence and skew be measured.

In addition, the present invention can be applied also to a checkup/measuring apparatus for measuring another characteristics of an optical disk.

In particular, in the case where measurement can be made while an optical disk to be measured is being rotated and driven and a large number of measuring points in the radial direction R is not required very much, this checkup/measuring apparatus can be used for check and measurement of external characteristics such as a warp and waviness of an optical disk, and a distribution of a thickness and the like.

As in the case where characteristics such as reflectance and the like of recording pits of the optical disk to be measured are checked while tracking a recording track, since it is necessary to move the optical system to the radial direction so as to track the recording track, it is difficult to apply the present invention to this case.

The optical disk checkup/measuring apparatus of the present invention is not limited to the above embodiments, and it may be varied in many ways within the scope of the invention.

According to the optical disk checkup/measuring apparatus of the present invention, the light emitting portion is composed of a plurality of light emitting elements arranged in the radial direction of the optical disk, and the optical disk to be measured is rotated by rotation driving means so that the measurement is repeated. As a result, the measurement of the whole periphery of the optical disk to be measured can be made.

As a result, the speed of the measurement of the characteristics such as birefringence and skew is increased.

Therefore, the optical disk checkup/measuring apparatus can be installed in the optical disk manufacturing apparatus so that the number of the steps of the check can be reduced and a defect can be found earlier.

In addition, since a moving mechanism of the optical system is not required, the structure of the checkup/measuring apparatus is simplified.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. An optical disk checkup/measuring apparatus comprising:
    rotation driving means for rotatably driving an optical disk to be measured;
    a light emitting portion formed of a plurality of light emitting elements arranged in a radial direction of said disk to be measured and fixed to prevent movement thereof for emitting a respective plurality of light beams successively one at a time onto said optical disk to be measured, so that the plurality of light beams are reflected by said optical disk to be measured;
    a fixed optical detecting portion for receiving and detecting the light beam reflected from said optical disk to be measured; and
    an operation processing portion for processing a signal output from said fixed optical detecting portion so as to form a specified signal, wherein at least one of birefringence and skew is measured for said optical disk to be measured by said operation processing portion.

2. The optical disk checkup/measuring apparatus according to claim 1, further comprising means for exciting the plurality of light emitting elements one by one from one radial direction so that the light beams are emitted successively from the plurality of light emitting elements onto said optical disk to be measured.

3. An optical disk checkup/measuring apparatus comprising:
    rotation driving means for rotatably driving an optical disk to be measured;
    a light emitting portion formed of a plurality of light emitting elements arranged in a radial direction of said disk to be measured and fixed to prevent movement thereof for emitting a respective plurality of light beams successively one at a time onto said optical disk to be measured, so that the plurality of light beams are reflected by said optical disk to be measured;
    a fixed optical detecting portion for receiving and detecting the light beam reflected from said optical disk to be measured;
    an operation processing portion for processing a signal output from said fixed optical detecting portion so as to form a specified signal; and
    shutters provided between said fixed light emitting portion and said optical disk to be measured, and said shutters are opened and closed so that all of the plurality of light emitting elements emit the light beams and so that the light beams are successively emitted from each of the light emitting elements onto said optical disk to be measured.

* * * * *